US008252976B2

(12) United States Patent
Hellwege et al.

(10) Patent No.: US 8,252,976 B2
(45) Date of Patent: Aug. 28, 2012

(54) SUGARCANE PLANTS WITH AN INCREASED STORAGE CARBOHYDRATE CONTENT

(75) Inventors: Elke Hellwege, Berlin (DE); Karola Knuth, Berlin (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 12/862,254

(22) Filed: Aug. 24, 2010

(65) Prior Publication Data
US 2011/0061131 A1 Mar. 10, 2011

Related U.S. Application Data

(62) Division of application No. 11/793,031, filed as application No. PCT/EP2005/014063 on Dec. 21, 2005, now Pat. No. 7,807,871.

(60) Provisional application No. 60/637,918, filed on Dec. 21, 2004.

(30) Foreign Application Priority Data

Dec. 21, 2004 (EP) .................................... 04090502

(51) Int. Cl.
| C12N 15/54 | (2006.01) |
| C12N 15/11 | (2006.01) |
| C12N 15/29 | (2006.01) |
| C12N 15/63 | (2006.01) |
| C12N 15/82 | (2006.01) |

(52) U.S. Cl. ..... 800/284; 800/278; 800/298; 435/320.1; 435/468; 536/23.1; 536/23.2; 536/23.6

(58) Field of Classification Search .......................... None
See application file for complete search history.

(56) References Cited

U.S. PATENT DOCUMENTS

| 6,664,444 B1 * | 12/2003 | Koops et al. .................. 800/284 |
| 2003/0041357 A1 | 2/2003 | Jepson et al. |
| 2004/0064852 A1 | 4/2004 | Weyens et al. |

FOREIGN PATENT DOCUMENTS

| WO | WO 96/01904 | 1/1996 |
| WO | WO 96/21023 | 7/1996 |
| WO | WO 98/39460 | 8/1998 |

OTHER PUBLICATIONS

Liu et al., Plant Molecular Biology, vol. 165 (2003).
Snyman et al., Acta Horticulturae, vol. 560, pp. 105-108 (2001).
Arencibia et al., Transgenic Research, vol. 7, pp. 213-222 (1998).
Beck et al. GenBank Accession No. V00618 "Transposon Tn5 Fragment Encoding Neomycin and Kanamycin Resistance (neo) and a Fragment of the Reading Frame of a Further Protein." (2005).
Beck et al., Gene, vol. 19, pp. 327-336 (1982).
Bower et al., The Plant Journal, vol. 2, No. 3, pp. 409-416, (1992).
Bower et al., Molecular Breeding, vol. 2, No. 3, pp. 239-249 (1996).
Callis et al., Genes and Development, vol. 1, pp. 1183-1200, (1987).
Chalmers et al., Journal of Plant Physiology, vol. 160, No. 11, pp. 1385-1391 (2003).
Christensen et al., Plant Molecular Biology, vol. 18, pp. 675-689 (1992).
Franks et al., Australian Journal of Plant Physiology, vol. 18, pp. 471-480 (1991).
Gallo-Meagher et al. , Cropscience, vol. 36, No. 5, pp. 1367-1374 (1967).
Hellwege et al. "Transgenic Potato (*Solanum tuberosum*) Tubers Synthesize the Full Spectrum of Insulin Molecules Naturally Occurring in Globe Artichoke (*Cynara scolymus*) Roots." Proc. Natl. Acad. Sci., vol. 97, No. 15, pp. 8699-8704 (2000).
Hellwege et al. GenBank Accession No. AJ000481 "*Cynara scolymus* mRNA for Fructan Fructan 1-Fructosyltransferase" (2002).
Hellwege et al., FEBS Letters, vol. 427, pp. 25-28 (1998).
Hellwege et al., Plant Journal, vol. 12, pp. 1057-1065 (1997).
Ho et al., Annals of Botany, vol. 51, pp. 719-726 (1983).
Kawakami et al., Bioscience, Biotechnology and Biochemistry, vol. 66, No. 11, pp. 2297-2305 (2002).
Last et al., Theoretical and Applied Genetics, vol. 81, pp. 581-588 (1991).
Luehrsen et al., Molecular Genetics and Genomics, vol. 225, pp. 81-93 (1991).
Lüscher et al., Plant Physiology, vol. 124, No. 3, pp. 1217-1228 (2000).
McElroy et al., Plant Cell, vol. 2, pp. 163-172 (1990).
Nagaraj et al., New Phytologist, vol. 161, No. 3, pp. 735-748 (2004).
Odell et al., Nature, vol. 313, pp. 810-812 (1985).
Rethmeier et al., Plant Journal, vol. 12, No. 4, pp. 895-899 (1997).
Rose et al., Plant Journal, vol. 11, pp. 455-464 (1997).
Rose et al., Plant Physiology, vol. 122, No. 2, pp. 535-542 (2000).
Schenk et al., Plant Molecular Biology, vol. 47, pp. 399-412 (2001).
Sevenier et al., Nature Biotechnology, vol. 16, pp. 843-846 (1998).
Snyman et al., South African Journal of Botany, vol. 62, No. 3, pp. 151-154 (1996).
Van Der Meer et al., Plant Journal, vol. 15, No. 4, pp. 489-500 (1998).
Vasil et al., Plant Physiology, vol. 91, pp. 1575-1579 (1989).
Vijn et al., Plant Journal, vol. 11, No. 3, pp. 387-398 (1997).
Vijn et al., Plant Physiology, vol. 117, No. 4, pp. 1507-1513 (1998).
Vijn et al., Plant Physiology, vol. 120, pp. 351-359 (1999).
Wei et al., Journal of Plant Physiology, vol. 159, No. 7, pp. 705-715 (2002).
Werr et al., EMBO Journal, vol. 4, pp. 1373-1380 (1985).
Wie et al., Journal of Plant Physiology, vol. 158, pp. 1203-1213 (2001).
Xu et al., Science in China Series C, vol. 46, No. 6, pp. 561-569, (2003).
International Preliminary Report on Patentability for International Application No. PCT/EP2005/014063 completed on Jan. 11, 2007.
International Search Report for International Application No. PCT/EP2005/014063 mailed Sep. 11, 2006.
Written Opinion for International Application No. PCT/EP2005/014063 mailed Sep. 11, 2006.

* cited by examiner

*Primary Examiner* — Brent T Page
(74) *Attorney, Agent, or Firm* — Hunt & Williams, LLP

(57) ABSTRACT

The present invention relates to a method for increasing the storage carbohydrate content of sugarcane plants.

1 Claim, 2 Drawing Sheets

Storage carbohydrate (sucrose + fructan) content in stalks of transgenic sugarcane plants Storage carbohydrate (sucrose + fructan) content in transgenic sugarcane plants/harvest 2003

SEQUENCE LISTING

```
<160> NUMBER OF SEQ ID NOS: 11

<210> SEQ ID NO 1
<211> LENGTH: 637
<212> TYPE: PRT
<213> ORGANISM: Cynara scolymus
<300> PUBLICATION INFORMATION:
<308> DATABASE ACCESSION NUMBER: CAA70855
<309> DATABASE ENTRY DATE: 1997-10-09
<313> RELEVANT RESIDUES IN SEQ ID NO: (1)..(637)

<400> SEQUENCE: 1

Met Ala Ser Ser Thr Thr Thr Pro Leu Leu Pro His His His Leu Gln
1               5                   10                  15

Asn Pro Gln Gln Leu Ala Gly Ser Pro Ala Ala His Arg Leu Ser Arg
            20                  25                  30

Pro Thr Leu Leu Ser Gly Ile Leu Val Ser Val Leu Val Ile Cys Ala
        35                  40                  45

Leu Val Ala Val Ile His Asn Gln Ser Gln Gln Pro Tyr His Asp Gly
    50                  55                  60

Gly Ala Lys Pro Ser Ser Ser Ala Ala Thr Thr Thr Phe Pro Thr Ala
65                  70                  75                  80

Ser Pro Glu Ala Gly Leu Lys Arg Phe Pro Ile Glu Leu Lys Thr Asn
                85                  90                  95

Ala Glu Val Glu Trp Gln Arg Ser Ala Tyr His Phe Gln Pro Asp Lys
            100                 105                 110

Asn Tyr Ile Ser Asp Pro Asp Gly Pro Met Tyr His Met Gly Trp Tyr
        115                 120                 125

His Leu Phe Tyr Gln Tyr Asn Pro Glu Ser Ala Ile Trp Gly Asn Ile
    130                 135                 140

Thr Trp Gly His Ser Val Ser Lys Asp Met Ile Asn Trp Phe His Leu
145                 150                 155                 160

Pro Phe Ala Met Val Pro Asp Gln Trp Tyr Asp Ile Glu Gly Val Met
                165                 170                 175

Thr Gly Ser Ala Thr Val Leu Pro Asp Gly Gln Ile Ile Met Leu Tyr
            180                 185                 190
```

Thr Gly Asn Ala Tyr Asp Leu Ser Gln Leu Gln Cys Leu Ala Tyr Ala
            195                 200                 205

Val Asn Ser Ser Asp Pro Leu Leu Asp Trp Lys Lys Tyr Glu Gly
    210                 215                 220

Asn Pro Ile Leu Phe Pro Pro Gly Val Gly Tyr Lys Asp Phe Arg
225                 230                 235                 240

Asp Pro Ser Thr Leu Trp Leu Gly Pro Asp Gly Glu Tyr Arg Met Val
                245                 250                 255

Met Gly Ser Lys His Asn Glu Thr Ile Gly Cys Ala Leu Ile Tyr His
            260                 265                 270

Thr Thr Asn Phe Thr His Phe Glu Leu Lys Glu Val Leu His Ala
        275                 280                 285

Val Pro His Thr Gly Met Trp Glu Cys Val Asp Leu Tyr Pro Val Ser
    290                 295                 300

Thr Thr His Thr Asn Gly Leu Asp Met Val Asp Asn Gly Pro Asn Val
305                 310                 315                 320

Lys His Val Leu Lys Gln Ser Gly Asp Glu Asp Arg His Asp Trp Tyr
                325                 330                 335

Ala Leu Gly Thr Tyr Asp Val Val Asn Asp Lys Trp Tyr Pro Asp Asp
            340                 345                 350

Pro Glu Asn Asp Val Gly Ile Gly Leu Arg Tyr Asp Phe Gly Lys Phe
        355                 360                 365

Tyr Ala Ser Lys Thr Phe Tyr Asp Gln His Lys Lys Arg Arg Val Leu
    370                 375                 380

Trp Gly Tyr Val Gly Glu Thr Asp Pro Pro Lys Tyr Asp Val Tyr Lys
385                 390                 395                 400

Gly Trp Ala Asn Ile Leu Asn Ile Pro Arg Thr Ile Val Leu Asp Thr
                405                 410                 415

Lys Thr Asn Thr Asn Leu Ile Gln Trp Pro Ile Ala Glu Val Glu Asn
            420                 425                 430

Leu Arg Ser Asn Lys Tyr Asn Glu Phe Lys Asp Val Glu Leu Lys Pro
        435                 440                 445

Gly Ser Leu Ile Pro Leu Glu Ile Gly Thr Ala Thr Gln Leu Asp Ile
    450                 455                 460

Thr Ala Thr Phe Glu Val Asp Gln Thr Met Leu Glu Ser Thr Leu Glu
465                 470                 475                 480

Ala Asp Val Leu Phe Asn Cys Thr Thr Ser Glu Gly Ser Ala Gly Arg
                485                 490                 495

Gly Val Leu Gly Pro Phe Gly Leu Val Val Leu Ala Asp Ala Glu Arg
            500                 505                 510

Ser Glu Gln Leu Pro Val Tyr Phe Tyr Ile Ala Lys Asp Thr Asp Gly
        515                 520                 525

Ser Ser Lys Thr Tyr Phe Cys Ala Asp Glu Ser Arg Ser Ser Asn Asp
    530                 535                 540

Val Asp Ile Gly Lys Trp Val Tyr Gly Ser Ser Val Pro Val Leu Glu
545                 550                 555                 560

Gly Glu Lys Phe Asn Met Arg Leu Leu Val Asp His Ser Ile Val Glu
                565                 570                 575

Gly Phe Ala Gln Gly Gly Arg Thr Val Val Thr Ser Arg Val Tyr Pro
            580                 585                 590

Ala Lys Ala Ile Tyr Gly Ala Ala Lys Leu Phe Leu Phe Asn Asn Ala
        595                 600                 605

Thr Gly Ile Ser Val Lys Ala Ser Leu Lys Ile Trp Lys Met Lys Glu

```
                    610                 615                 620

Ala Gln Leu Asp Pro Phe Pro Leu Ser Gly Trp Ser Ser
625                 630                 635

<210> SEQ ID NO 2
<211> LENGTH: 617
<212> TYPE: PRT
<213> ORGANISM: Cynara scolymus
<300> PUBLICATION INFORMATION:
<308> DATABASE ACCESSION NUMBER: CAA04120
<309> DATABASE ENTRY DATE: 2002-11-13
<313> RELEVANT RESIDUES IN SEQ ID NO: (1)..(617)

<400> SEQUENCE: 2

Met Arg Thr Thr Glu Pro Gln Thr Asp Leu Glu His Ala Pro Asn His
1               5                   10                  15

Thr Pro Leu Leu Asp His Pro Glu Pro Pro Ala Ala Val Arg Asn
            20                  25                  30

Arg Leu Leu Ile Arg Val Ser Ser Ile Thr Leu Val Ser Leu Phe
        35                  40                  45

Phe Val Ser Ala Phe Leu Leu Ile Leu Leu Tyr Gln His Asp Ser Thr
50                  55                  60

Tyr Thr Asp Asp Asn Ser Ala Pro Ser Glu Ser Ser Gln Gln Pro
65                  70                  75              80

Ser Ala Ala Asp Arg Leu Arg Trp Glu Arg Thr Ala Phe His Phe Gln
                85                  90                  95

Pro Ala Lys Asn Phe Ile Tyr Asp Pro Asn Gly Pro Leu Phe His Met
            100                 105                 110

Gly Trp Tyr His Leu Phe Tyr Gln Tyr Asn Pro Tyr Ala Pro Phe Trp
        115                 120                 125

Gly Asn Met Thr Trp Gly His Ala Val Ser Lys Asp Met Ile Asn Trp
130                 135                 140

Phe Glu Leu Pro Ile Ala Leu Ala Pro Thr Glu Trp Tyr Asp Ile Glu
145                 150                 155                 160

Gly Val Leu Ser Gly Ser Thr Thr Ile Leu Pro Asp Gly Arg Ile Phe
                165                 170                 175

Ala Leu Tyr Thr Gly Asn Thr Asn Asp Leu Glu Gln Leu Gln Cys Lys
            180                 185                 190

Ala Val Pro Val Asn Ala Ser Asp Pro Leu Leu Val Glu Trp Val Arg
        195                 200                 205

Tyr Asp Ala Asn Pro Ile Leu Tyr Ala Pro Ser Gly Ile Gly Leu Thr
210                 215                 220

Asp Tyr Arg Asp Pro Ser Thr Val Trp Thr Gly Pro Asp Gly Lys His
225                 230                 235                 240

Arg Met Ile Ile Gly Thr Lys Arg Asn Thr Thr Gly Leu Val Leu Val
                245                 250                 255

Tyr His Thr Thr Asp Phe Thr Asn Tyr Val Met Leu Asp Glu Pro Leu
            260                 265                 270

His Ser Val Pro Asn Thr Asp Met Trp Glu Cys Val Asp Leu Tyr Pro
        275                 280                 285

Val Ser Thr Thr Asn Asp Ser Ala Leu Asp Val Ala Ala Tyr Gly Pro
290                 295                 300

Gly Ile Lys His Val Leu Lys Glu Ser Trp Glu Gly His Ala Met Asp
305                 310                 315                 320

Phe Tyr Ser Ile Gly Thr Tyr Asp Ala Phe Asn Asp Lys Trp Thr Pro
                325                 330                 335
```

```
Asp Asn Pro Glu Leu Asp Val Gly Ile Gly Leu Arg Cys Asp Tyr Gly
            340                 345                 350

Arg Phe Phe Ala Ser Lys Ser Leu Tyr Asp Pro Leu Lys Lys Arg Arg
            355                 360                 365

Val Thr Trp Gly Tyr Val Ala Glu Ser Asp Ser Tyr Asp Gln Asp Val
            370                 375                 380

Ser Arg Gly Trp Ala Thr Ile Tyr Asn Val Ala Arg Thr Ile Val Leu
385                 390                 395                 400

Asp Arg Lys Thr Gly Thr His Leu Leu Gln Trp Pro Val Glu Glu Ile
            405                 410                 415

Glu Ser Leu Arg Ser Asn Gly His Glu Phe Lys Asn Ile Thr Leu Glu
            420                 425                 430

Pro Gly Ser Ile Ile Pro Leu Asp Val Gly Ser Ala Thr Gln Leu Asp
            435                 440                 445

Ile Val Ala Thr Phe Glu Val Asp Gln Glu Ala Leu Lys Ala Thr Ser
            450                 455                 460

Asp Thr Asn Asp Glu Tyr Gly Cys Thr Thr Ser Ser Gly Ala Ala Gln
465                 470                 475                 480

Arg Gly Ser Phe Gly Pro Phe Gly Ile Ala Val Leu Ala His Gly Thr
            485                 490                 495

Leu Ser Glu Leu Thr Pro Val Tyr Phe Tyr Ile Ala Lys Asn Thr Lys
            500                 505                 510

Gly Gly Val Asp Thr His Phe Cys Thr Asp Lys Leu Arg Ser Ser Tyr
            515                 520                 525

Asp Tyr Asp Gly Glu Lys Val Val Tyr Gly Ser Thr Val Pro Val Leu
530                 535                 540

Asp Gly Glu Glu Phe Thr Met Arg Ile Leu Val Asp His Ser Val Val
545                 550                 555                 560

Glu Gly Phe Ala Gln Gly Gly Arg Thr Val Ile Thr Ser Arg Val Tyr
            565                 570                 575

Pro Thr Lys Ala Ile Tyr Glu Ala Ala Lys Leu Phe Val Phe Asn Asn
            580                 585                 590

Ala Thr Thr Thr Ser Val Lys Ala Thr Leu Lys Val Trp Gln Met Ser
            595                 600                 605

Gln Ala Phe Val Lys Ala Tyr Pro Phe
            610                 615

<210> SEQ ID NO 3
<211> LENGTH: 612
<212> TYPE: PRT
<213> ORGANISM: Allium cepa
<300> PUBLICATION INFORMATION:
<308> DATABASE ACCESSION NUMBER: CAA69170
<309> DATABASE ENTRY DATE: 2004-09-09
<313> RELEVANT RESIDUES IN SEQ ID NO: (1)..(612)

<400> SEQUENCE: 3

Met Asp Ala Gln Asp Ile Glu Ser Arg His Pro Leu Ile Gly Ala Arg
1               5                   10                  15

Pro Arg Arg Arg Ala Leu Arg Ser Leu Ser Ile Leu Leu Ala Ala Ala
            20                  25                  30

Leu Leu Leu Gly Leu Val Leu Phe Tyr Ala Asn Gly Thr Gly Ser Gly
            35                  40                  45

Thr Ala Val Asp Pro Val Arg Val Asp Asn Glu Phe Pro Trp Thr Asn
50                  55                  60

Asp Met Leu Ala Trp Gln Arg Cys Gly Phe His Phe Arg Thr Val Arg
65                  70                  75                  80
```

```
Asn Tyr Met Asn Asp Pro Ser Gly Pro Met Tyr Tyr Lys Gly Trp Tyr
                 85                  90                  95

His Leu Phe Tyr Gln His Asn Lys Asp Phe Ala Tyr Trp Gly Asn Ile
            100                 105                 110

Thr Trp Gly His Ala Val Ser Arg Asp Leu Ile Asn Trp Gln His Leu
        115                 120                 125

Pro Val Ala Val Gly Pro Asp His Trp Tyr Asp Ile Ser Gly Val Trp
    130                 135                 140

Thr Gly Ser Ile Ile Val Val Ser Glu Asp Arg Val Val Met Leu Phe
145                 150                 155                 160

Thr Gly Gly Thr Lys Ser Phe Asp Gln Ser Ile Asn Leu Ala Glu Ala
                165                 170                 175

Ala Asp Pro Ser Asp Pro Leu Leu Lys Trp Ile Lys Tyr Asp Asn
                180                 185                 190

Asn Pro Ile Leu Trp Pro Pro Gly Ile Val Arg Asp Asp Phe Arg
            195                 200                 205

Asp Pro Asn Pro Ile Trp Tyr Asn Ala Ser Glu Ser Thr Tyr His Ile
    210                 215                 220

Val Val Gly Ser Lys Asn Asp Ser Leu Gln His Thr Gly Ile Ala Leu
225                 230                 235                 240

Val Tyr Leu Thr Lys Asp Phe Lys Lys Phe Asp Leu Leu Pro Thr Val
                245                 250                 255

Leu His Ser Val Asp Lys Val Gly Met Trp Glu Cys Val Glu Val Tyr
            260                 265                 270

Pro Val Ala Thr Thr Gly Pro Leu Leu His Lys Ala Ile Asp Asn Phe
        275                 280                 285

Asp Val Asp Arg Val Leu Asp Arg Ser Thr Val Lys His Val Leu Lys
    290                 295                 300

Ala Ser Met Asn Asp Glu Trp His Asp Tyr Tyr Ala Ile Gly Thr Phe
305                 310                 315                 320

Asp Pro Ile Gly Asn Lys Trp Thr Pro Asp Glu Thr Val Asp Val
                325                 330                 335

Gly Ile Gly Leu Arg Tyr Asp Trp Gly Lys Phe Tyr Ala Ser Arg Thr
            340                 345                 350

Phe Phe Asp Pro Leu Lys Gln Arg Arg Ile Ile Trp Gly Tyr Ile Gly
        355                 360                 365

Glu Val Asp Ser Gln Lys Ala Asp Ile Ala Lys Gly Trp Ala Ser Leu
    370                 375                 380

Gln Gly Ile Pro Arg Ser Val Leu Tyr Asp Val Lys Thr Gly Thr Asn
385                 390                 395                 400

Val Leu Thr Trp Pro Ile Glu Glu Met Glu Gly Leu Arg Met Ala Arg
                405                 410                 415

Lys Asp Phe Ser Gly Ile Lys Ile Lys Lys Gly Ser Thr Val Glu Leu
            420                 425                 430

Ser Asp Phe Gly Asp Ala Phe Gln Ile Asp Ile Glu Ala Glu Phe Thr
        435                 440                 445

Ile Ser Lys Glu Ala Leu Glu Ala Thr Ile Glu Ala Asp Val Gly Tyr
    450                 455                 460

Asn Cys Ser Ser Ser Gly Gly Ala Ala Ile Arg Gly Thr Leu Gly Pro
465                 470                 475                 480

Phe Gly Leu Leu Val Leu Ala Asn Gln Asp Leu Thr Glu Asn Thr Ala
                485                 490                 495

Thr Tyr Phe Tyr Val Ser Lys Gly Ile Asp Gly Ser Leu Ile Thr His
```

```
                        500                 505                 510
        Phe Cys Gln Asp Glu Thr Arg Ser Ser Lys Ala Asn Asp Ile Val Lys
                    515                 520                 525

Arg Val Val Gly Gly Thr Val Pro Val Leu Asp Gly Glu Thr Phe Ala
                530                 535                 540

Val Arg Ile Leu Val Asp His Ser Val Ile Glu Ser Phe Ala Met Gly
        545                 550                 555                 560

Gly Arg Thr Ser Ala Thr Ser Arg Ala Tyr Pro Thr Glu Ala Ile Asn
                        565                 570                 575

Ser Ala Ala Arg Val Phe Leu Phe Asn Asn Ala Thr Gly Val Asp Val
                    580                 585                 590

Ile Ala Glu Ser Val Lys Ile Trp Gln Met Asn Ser Thr Tyr Asn Asp
                    595                 600                 605

Phe Tyr His Phe
                610

<210> SEQ ID NO 4
<211> LENGTH: 625
<212> TYPE: PRT
<213> ORGANISM: Hordeum vulgare
<300> PUBLICATION INFORMATION:
<308> DATABASE ACCESSION NUMBER: T06184
<309> DATABASE ENTRY DATE: 2000-07-21
<313> RELEVANT RESIDUES IN SEQ ID NO: (1)..(625)

<400> SEQUENCE: 4

Met Gly Ser His Gly Lys Pro Pro Leu Pro Tyr Ala Tyr Lys Pro Leu
1               5                   10                  15

Pro Ser Asp Ala Ala Asp Gly Lys Arg Thr Gly Cys Met Arg Trp Ser
            20                  25                  30

Ala Cys Ala Thr Val Leu Thr Ala Ser Ala Met Ala Val Val Val
        35                  40                  45

Gly Ala Thr Leu Leu Ala Gly Leu Arg Met Glu Gln Ala Val Asp Glu
    50                  55                  60

Glu Ala Ala Ala Gly Gly Phe Pro Trp Ser Asn Glu Met Leu Gln Trp
65                  70                  75                  80

Gln Arg Ser Gly Tyr His Phe Gln Thr Ala Lys Asn Tyr Met Ser Asp
                85                  90                  95

Pro Asn Gly Leu Met Tyr Tyr Arg Gly Trp Tyr His Met Phe Tyr Gln
            100                 105                 110

Tyr Asn Pro Val Gly Thr Asp Trp Asp Asp Gly Met Glu Trp Gly His
        115                 120                 125

Ala Val Ser Arg Asn Leu Val Gln Trp Arg Thr Leu Pro Ile Ala Met
    130                 135                 140

Val Ala Asp Gln Trp Tyr Asp Ile Leu Gly Val Leu Ser Gly Ser Met
145                 150                 155                 160

Thr Val Leu Pro Asn Gly Thr Val Ile Met Ile Tyr Thr Gly Ala Thr
                165                 170                 175

Asn Ala Ser Ala Val Glu Val Gln Cys Ile Ala Thr Pro Ala Asp Pro
            180                 185                 190

Asn Asp Pro Leu Leu Arg Arg Trp Thr Lys His Pro Ala Asn Pro Val
        195                 200                 205

Ile Trp Ser Pro Pro Gly Val Gly Thr Lys Asp Phe Arg Asp Pro Met
    210                 215                 220

Thr Ala Trp Tyr Asp Glu Ser Asp Glu Thr Trp Arg Thr Leu Leu Gly
225                 230                 235                 240
```

-continued

Ser Lys Asp Asp His Asp Gly His His Asp Gly Ile Ala Met Met Tyr
            245                 250                 255

Lys Thr Lys Asp Phe Leu Asn Tyr Glu Leu Ile Pro Gly Ile Leu His
            260                 265                 270

Arg Val Val Arg Thr Gly Glu Trp Glu Cys Ile Asp Phe Tyr Pro Val
            275                 280                 285

Gly Arg Arg Ser Ser Asp Asn Ser Ser Glu Met Leu His Val Leu Lys
            290                 295                 300

Ala Ser Met Asp Asp Glu Arg His Asp Tyr Tyr Ser Leu Gly Thr Tyr
305                 310                 315                 320

Asp Ser Ala Ala Asn Thr Trp Thr Pro Ile Asp Pro Glu Leu Asp Leu
            325                 330                 335

Gly Ile Gly Leu Arg Tyr Asp Trp Gly Lys Phe Tyr Ala Ser Thr Ser
            340                 345                 350

Phe Tyr Asp Pro Ala Lys Asn Arg Arg Val Leu Met Gly Tyr Val Gly
            355                 360                 365

Glu Val Asp Ser Lys Arg Ala Asp Val Val Lys Gly Trp Ala Ser Ile
            370                 375                 380

Gln Ser Val Pro Arg Thr Val Ala Leu Asp Glu Lys Thr Arg Thr Asn
385                 390                 395                 400

Leu Leu Leu Trp Pro Val Glu Ile Glu Thr Leu Arg Leu Asn Ala
            405                 410                 415

Thr Glu Leu Thr Asp Val Thr Ile Asn Thr Gly Ser Val Ile His Ile
            420                 425                 430

Pro Leu Arg Gln Gly Thr Gln Leu Asp Ile Glu Ala Ser Phe His Leu
            435                 440                 445

Asp Ala Ser Ala Val Ala Ala Leu Asn Glu Ala Asp Val Gly Tyr Asn
450                 455                 460

Cys Ser Ser Ser Gly Gly Ala Val Asn Arg Gly Ala Leu Gly Pro Phe
465                 470                 475                 480

Gly Leu Leu Val Leu Ala Ala Gly Asp Arg Arg Gly Glu Gln Thr Ala
            485                 490                 495

Val Tyr Phe Tyr Val Ser Arg Gly Leu Asp Gly Gly Leu His Thr Ser
            500                 505                 510

Phe Cys Gln Asp Glu Leu Arg Ser Ser Arg Ala Lys Asp Val Thr Lys
            515                 520                 525

Arg Val Ile Gly Ser Thr Val Pro Val Leu Asp Gly Glu Ala Leu Ser
            530                 535                 540

Met Arg Val Leu Val Asp His Ser Ile Val Gln Gly Phe Asp Met Gly
545                 550                 555                 560

Gly Arg Thr Thr Met Thr Ser Arg Val Tyr Pro Met Glu Ser Tyr Gln
            565                 570                 575

Glu Ala Arg Val Tyr Leu Phe Asn Asn Ala Thr Gly Ala Ser Val Thr
            580                 585                 590

Ala Glu Arg Leu Val Val His Glu Met Asp Ser Ala His Asn Gln Leu
            595                 600                 605

Ser Asn Glu Asp Asp Gly Met Tyr Leu His Gln Val Leu Glu Ser Arg
            610                 615                 620

His
625

<210> SEQ ID NO 5
<211> LENGTH: 27
<212> TYPE: DNA
<213> ORGANISM: Artificial Sequence

```
<220> FEATURE:
<223> OTHER INFORMATION: PCR Primer

<400> SEQUENCE: 5
aattcagctg ttatccctag gcggacc                                         27

<210> SEQ ID NO 6
<211> LENGTH: 32
<212> TYPE: DNA
<213> ORGANISM: Artificial Sequence
<220> FEATURE:
<223> OTHER INFORMATION: PCR Primer

<400> SEQUENCE: 6
agtcagctgg gaatttaaat ttaattaagg cg                                   32

<210> SEQ ID NO 7
<211> LENGTH: 31
<212> TYPE: DNA
<213> ORGANISM: Artificial Sequence
<220> FEATURE:
<223> OTHER INFORMATION: PCR Primer

<400> SEQUENCE: 7
aaaatttaaa cataatcagg atcaataaaa c                                    31

<210> SEQ ID NO 8
<211> LENGTH: 27
<212> TYPE: DNA
<213> ORGANISM: Artificial Sequence
<220> FEATURE:
<223> OTHER INFORMATION: PCR Primer

<400> SEQUENCE: 8
aaaatttaaa catctgcgct tactcct                                         27

<210> SEQ ID NO 9
<211> LENGTH: 47
<212> TYPE: DNA
<213> ORGANISM: Artificial Sequence
<220> FEATURE:
<223> OTHER INFORMATION: PCR Primer

<400> SEQUENCE: 9
acttctgcag cggccgcgat cgttcaaaca tttggcaata aagtttc                   47

<210> SEQ ID NO 10
<211> LENGTH: 50
<212> TYPE: DNA
<213> ORGANISM: Artificial Sequence
<220> FEATURE:
<223> OTHER INFORMATION: PCR Primer

<400> SEQUENCE: 10
tctaagcttg gcgccgctag cagatctgat ctagtaacat agatgacacc                50

<210> SEQ ID NO 11
<211> LENGTH: 23
<212> TYPE: DNA
<213> ORGANISM: Artificial Sequence
<220> FEATURE:
<223> OTHER INFORMATION: PCR Primer

<400> SEQUENCE: 11
ggtaactgtc agaccaagtt tac                                             23
```

SUGARCANE PLANTS WITH AN INCREASED STORAGE CARBOHYDRATE CONTENT

CROSS-REFERENCE TO RELATED APPLICATIONS

This application is a divisional of U.S. patent application Ser. No. 11/793,031, filed Jun. 15, 2007, now U.S. Pat. No. 7,807,871 which is the U.S. national stage application of PCT/EP2005/014063, filed Dec. 21, 2005, which claims priority to EP 040 90 502.8, filed Dec. 21, 2004, and U.S. Provisional Patent Application No. 60/637,918, filed Dec. 21, 2004, the disclosures of each of which is hereby incorporated by reference.

BACKGROUND OF THE INVENTION (i) Field of the Invention

The present invention relates to a method for increasing the storage carbohydrate content of sugarcane plants.

(ii) Description of the Related Art

Those involved in the fields of agriculture and forestry constantly strive to provide higher-yielding plants, in particular to safeguard the food supply of the continuously increasing world population and to ensure the supply of renewable raw materials. A traditional attempt is to maintain high-yielding plants by means of breeding. However, this procedure is time- and labor-consuming. In some cases, progress has already been made by subjecting plants to genetic manipulation, i.e. by the directed introduction and expression of foreign (recombinant) nucleic acid molecules in/into plants.

Besides sugar beet, sugarcane is the most important plant used for the production of sugar (sucrose). To obtain cane sugar, the sugarcane is harvested in an expensive fabrication procedure and then transported to the factory. Prior to the extraction of the sugar, the sugarcane is cleaned. In the traditional method, the sugarcane is subsequently comminuted and then passes through 4-6 roller presses to separate the juice from the fiber (bagasse). The crystallized and centrifuged sugar (sucrose) is obtained by clarification, evaporation, fractional crystallization and separating the mother liquor (molasses) from the crystals by centrifugation. The molasses, is currently the economically most important by-product of obtaining sugar from sugarcane, comprise approximately 50% sugars (sucrose and monosaccharides). They are used as starting material for fermentation products, of which ethanol is the most important, and moreover as animal feed and, in some countries, also for human nutrition ("black honey" in Egypt).

Current biotechnological methods allow the generation of sugarcane plants which, besides cane sugar (sucrose) and molasses, synthesize valuable storage carbohydrates such as, for example, fructans, which can subsequently be employed for industrial, cosmetic or pharmaceutical purposes and in the food industry.

Thus, for example, the international patent applications WO96/01904, WO96/21023, WO98/39460 and WO99/24593 propose to express 1-SST genes alone or in combination with 1-FFT genes in sugarcane in order to produce fructans in transgenic sugarcane.

Obtaining storage carbohydrates (sucrose and fructans) from sugarcane plants in an efficient manner requires methods which lead to increasing the storage carbohydrate content in sugarcane plants.

SUMMARY OF THE PREFERRED EMBODIMENTS OF THE INVENTION

The present invention is thus based on the object of providing methods which lead to an increased storage carbohydrate content in sugarcane plants in comparison with conventional sugarcane plants.

This object is achieved by providing the embodiments specified in the patent claims.

The present invention thus relates to a method for increasing the storage carbohydrate content of a sugarcane plant, which comprises
(a) the genetic modification of a sugarcane plant by introducing at least one foreign nucleic acid molecule encoding a fructosyl transferase;
(b) the genetically modified sugarcane plant according to (a) having an increased storage carbohydrate content in comparison with corresponding non-genetically-modified sugarcane wild-type plants.

DETAILED DESCRIPTION OF THE PREFERRED EMBODIMENTS OF THE INVENTION

Figure 1:
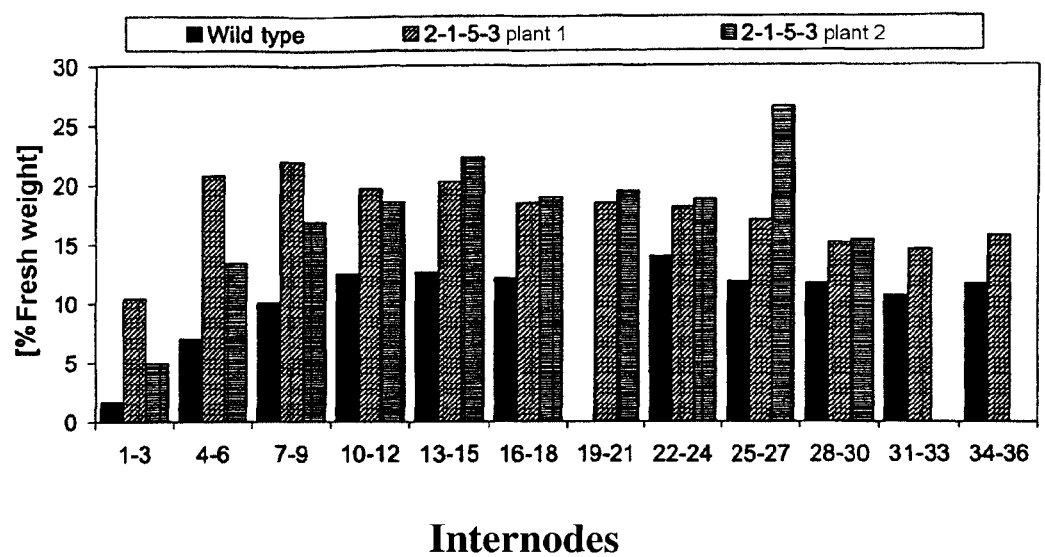
FIG. 1: Storage carbohydrate (sucrose and fructan) content in sugarcane stalks of the wild type NCo310 and of the transgenic oligofructan-synthetizing line 2-1-5-3. Material of three adjacent internodes was combined to give one sample. The internodes were numbered from top (=1) to bottom (=36).

For the purposes of the present invention, the term "storage carbohydrate content" is understood as meaning the total of the sucrose and fructan content per gram fresh weight.

For the purposes of the present invention, the terms "increasing the storage carbohydrate content" or "increased storage carbohydrate content" mean increasing the content of the total of sucrose and fructan per gram fresh weight by in total 2-100%, preferably by 5-80% and especially preferably by 10-65%.

In the context of the present invention, the sucrose or fructan content is preferably determined by the methods described further below in the methodology section.

In a further embodiment, the present invention relates to a method for increasing the total carbohydrate content of a sugarcane plant, which comprises
(a) the genetic modification of a sugarcane plant by introducing at least one foreign nucleic acid molecule encoding a fructosyl transferase;
(b) the genetically modified sugarcane plant according to (a) having an increased total carbohydrate content in comparison with corresponding non-genetically-modified sugarcane wild-type plants.

In the context of the present invention, the term "total carbohydrate content" is understood as meaning the total of the carbohydrates glucose, fructose, sucrose and fructan content per gram fresh weight.

In the context of the present invention, the terms "increasing the total carbohydrate content" or "increased total carbohydrate content" mean increasing the content of the total of carbohydrated glucose, fructose, sucrose and fructan per gram fresh weight by in total 5-100%, preferably by 8-80% and especially preferably by 11-66%.

In the context of the present invention, the glucose, fructose, sucrose or fructan content is preferably determined by the methods described further below in the methodology section.

In the context of the present invention, the fresh weight of the sugarcane plants is determined using conventional scales, by measuring the weight of all of the above-ground stem of a sugarcane plant after removing the leaves entirely.

It was surprising for the skilled worker that the expression of a plant fructosyl transferase gene in sugarcane plants not only leads to the synthesis of fructan, but the storage carbohydrate (sucrose+fructan) content also increases simultaneously. On the basis of the data regarding the expression of a 1-SST gene in sugar beet (Sevenier et al., Nature Biotechnology 16, (1998), 843), which show that the transgenic sugar beet plants show a reduced storage carbohydrate content (sucrose+fructan), a reduced total carbohydrate (sucrose+fructan+glucose+fructose) content and a significantly reduced sucrose content (<10% of the wild type) in comparison with corresponding sugar beet wild-type plants, the skilled worker would have expected that the corresponding approach in sugarcane likewise leads to a reduced storage carbohydrate and total carbohydrate content and to a significantly reduced sucrose content.

Surprisingly, however, these effects (reduced storage carbohydrate and total carbohydrate content) are not observed in sugarcane. In contrast, the storage carbohydrate and total carbohydrate contents of the transgenic sugarcane plants even exceed those of the corresponding wild-type plants. Also, the genetically modified sugarcane plants of the method according to the invention show no reduced sucrose content down to 10% of the wild-type level in comparison with corresponding, non-genetically-modified sugarcane wild-type plants.

This surprising effect is of enormous commercial importance since the method according to the invention allows sugarcane plants to be employed in the future for obtaining two raw materials, viz. cane sugar and fructan, without the cane sugar yield being significantly lowered.

In a further embodiment of the method according to the invention, the genetically modified sugarcane plants have an increased storage and/or total carbohydrate content in comparison with corresponding non-genetically-modified sugarcane wild-type plants and the sucrose content of the genetically modified sugarcane plants in comparison with the sucrose content of corresponding non-genetically-modified sugarcane wild-type plants amounts to more than 15% of the sucrose content of corresponding non-genetically-modified sugarcane wild-type plants, preferably to 20-130% and especially preferably to 30-100%.

In a further embodiment, the present invention thus relates to a method for increasing the storage carbohydrate content of a sugarcane plant, which comprises
(a) the genetic modification of a sugarcane plant by introducing at least one foreign nucleic acid molecule encoding a fructosyl transferase;
(b) the genetically modified sugarcane plant according to (a) having an increased storage carbohydrate content in comparison with corresponding non-genetically-modified sugarcane wild-type plants between the internodes 10-18.

In the context of the present invention, the term "increased storage carbohydrate content between the internodes 10-18" means that the sucrose and fructan content per gram fresh weight in the area between the internodes 10 and 18 is increased in total by at least 5%, in particular by 5-90%, preferably by 10-80% and especially preferably by 15-75%.

In the context of the present invention, the internodes of the stalk are numbered from top (=1) to bottom (for example =36). In the context of the present invention, an "internode" refers, in a sugarcane plant, to the portion of the shoot axis between two nodes (where the leaves grow from).

In this context, the term "sucrose and fructan content per gram fresh weight in the area between the internodes 10-18" is understood as meaning that the total of the sucrose and fructan contents and of the fresh weight of the stem after removal of the leaves in the stem region between internode 10 and internode 18 are determined.

In the context of the present invention, the term "sugarcane plant" is understood as meaning a plant of the genus *Saccharum*, preferably the species *Saccharum officinarum*.

In the context of the present invention, the term "genetic modification" or "genetically modified" means the introduction of at least one "foreign nucleic acid molecule" encoding a fructosyl transferase into the genome of a sugarcane plant cell or into the genome of a sugarcane plant, where said introduction of at least one foreign nucleic acid molecule results in the sugarcane plant synthesizing fructan. Sugarcane plants which do not have this genetic modification store no fructan, or at least in amounts which are so small that the fructan is not detectable, preferably by the method described further below in the methodology section ("fructan determination").

In the context of the present invention, the storage carbohydrate or total carbohydrate content determination should be carried out on sugarcane plants which have at least 10 internodes and which are at least 6, preferably 10-18, especially preferably 15 months old.

In the context of the present invention, the term "foreign nucleic acid molecule" is understood as meaning a molecule, preferably a heterologous molecule, which either does not occur naturally in corresponding non-genetically-modified sugarcane wild-type plants/plant cells, or which does not naturally occur in sugarcane wild-type plants/plant cells in this specific spatial arrangement or which is located at a location in the genome of the sugarcane wild-type plants/plant cell where it does not occur naturally.

Furthermore, the sugarcane plants/plant cells employed in the method according to the invention are distinguished from sugarcane wild-type plants/plant cells by the fact that they comprise at least one copy of the foreign nucleic acid molecule stably integrated into their genome, if appropriate in addition to copies of such a molecule which occur naturally in the sugarcane wild-type plants/plant cells. In this case, the sugarcane plants/plant cells of the method according to the invention can be distinguished from sugarcane wild-type plants/plant cells in particular by the fact that this additional copy, or these additional copies, is/are located at locations in the genome where it does not occur, or where they do not occur, in sugarcane wild-type plants/plant cells. This can be tested for example with the aid of a Southern blot analysis.

Moreover, the sugarcane plants/plant cells employed in the method according to the invention can be distinguished from sugarcane wild-type plants/plant cells preferably by at least one of the following features: if the foreign nucleic acid molecule which has been introduced is heterologous with regard to the plant cell or plant, transcripts of the nucleic acid molecules which have been introduced are present in the sugarcane plants/plant cells employed in the method according to the invention.

These nucleic acid molecules can be detected for example by Northern blot analysis or by RT-PCR (Reverse Transcription Polymerase Chain Reaction).

Furthermore, the sugarcane plants/plant cells employed in the method according to the invention form a protein which is encoded by a foreign nucleic acid molecule which has been introduced. This protein can be detected for example by immunological methods, in particular by a Western blot analysis.

In the context of the present invention, the term "genome" is to be understood as meaning the totality of the hereditary material present in a plant cell. The skilled worker knows that not only the nucleus, but also other cell compartments (for example plastids, mitochondria) comprise hereditary material.

The foreign nucleic acid molecule is preferably a recombinant molecule which consists of a variety of elements whose combination, or specific spatial arrangement, does not occur naturally in plant cells.

In principle, the foreign nucleic acid molecule can be any nucleic acid molecule which encodes at least one fructosyl transferase and which, in the sugarcane plant cell or sugarcane plant, leads to the sugarcane plant synthesizing fructan.

In the context of the present invention, the term "sugarcane wild-type plant cell" means sugarcane plant cells which have acted as starting material for the method according to the invention, i.e. whose genome is not modified by the introduction of at least one foreign nucleic acid molecule encoding at least one fructosyl transferase.

In the context of the present invention, the term "sugarcane wild-type plant" means plants which have acted as starting material for the method according to the invention, i.e. whose genome is not modified by the introduction of at least one foreign nucleic acid molecule encoding at least one fructosyl transferase.

In the context of the present invention, the term "corresponding" means that, when comparing a plurality of objects, the objects in question which are compared with one another are maintained under identical conditions. In the context of the present invention, the term "corresponding" in the context of sugarcane wild-type plant cell or sugarcane wild-type plant means that the sugarcane plant cells or sugarcane plants which are compared with each other were grown under identical culture conditions and have the same age, or spent the same time in culture.

In the context of the present invention, the term "fructosyl transferase" refers to plant enzymes which catalyze the synthesis of fructans in plant cells and which are also referred to as fructosyl transferases. The group of the plant fructosyl transferases includes:
 sucrose: sucrose 1-fructosyl transferases (1-SST) (EC 2.4.1.99),
 fructan: fructan 1-fructosyl transferases (1-FFT) (EC 2.4.1.100),
 fructan: fructan 6G-fructosyl transferases (6G-FFT) (E.C. 2.4.1.-) and
 sucrose: fructan 6-fructosyl transferases (6-SFT) (E.C. 2.4.1.10).

1-SSTs catalyze the synthesis of oligofructans (DP3-DP8) with beta-2,1-glycosidic bonds starting from the substrate sucrose. 1-SSTs catalyze the following reaction:

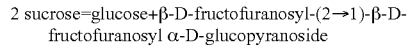

1-SST have encoding sequences from different organisms known to the skilled worker and available for example under the following NCBI GenBank Accession numbers:

*Allium cepa* AJ006066.1 (Vijn, I. et al., Plant Physiol. 117(4), (1998), 1507-1513); *Triticum aestivum* AB029888.1 (Kawakami, A. and Yoshida, M., Biosci. Biotechnol. Biochem. 66 (11), (2002), 2297-2305); *Allium sativum* AY098442.1; *Lolium perenne* AY245431.1 (Chalmers et al., J Plant Physiol. 160(11), (2003), 1385-91); *Festuca arundinacea* AJ297369.1, Luescher et al., Plant Physiol. 124 (3), (2000), 1217-1228); *Hordeum vulgare* AJ 567377.2, Nagaraj et al., New Phytologist. 161(3), (2004), 735-748); *Taraxacum officinale* AS250634.1, van den Ende et al., Plant Physiol. 123, (2000), 71-80.

Especially preferred in the context of the present invention is the 1-SST from *Cynara scolymus* (SEQ ID No. 1) or from *Helianthus tuberosus* (see WO96/21023, FIG. 4 (A), GenBank Acc. No. AJ009757.1, van der Meer et al., Plant J. 15(4), (1998), 489-500).

1-FFTs catalyze the synthesis of longer-chain beta-2,1-linked fructans of the inulin type which can have a degree of polymerization of up to DP=200, by transferring fructose units from existing oligofructan chains to other fructans or else sucrose. 1-FFTs catalyze the following reaction:

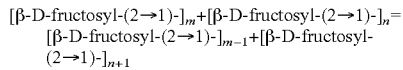

in addition to [β-D-fructosyl-(2→1)-]$_n$, sucrose may also act as acceptor for the beta-2,1-linked fructose residue in the above reaction.

1-FFT-encoding sequences from different organisms are known to the skilled worker and available for example under the following GenBank Accession numbers:
*Cichorium intybus* U84398.1.

Especially preferred in the context of the present invention is the 1-FFT from *Cynara scolymus* (SEQ ID No. 2) or from *Helianthus tuberosus* (see WO96/21023, FIG. 4(B), GenBank Acc. No. AJ009756.1, van der Meer et al. (Plant J. 15(4), (1998), 489-500).

In a further preferred embodiment of the method according to the invention, a further foreign nucleic acid molecule encoding an FFT is introduced into the genome of the sugarcane plant, in addition to the foreign nucleic acid molecule which encodes a 1-SST. This means to say that, in this embodiment of the method according to the invention, a first foreign nucleic acid molecule encodes a 1-SST and a second foreign nucleic acid molecule a 1-FFT.

The foreign nucleic acid molecules introduced into the sugarcane plant cell or sugarcane plant for the purposes of genetic modification may take the form of a single nucleic acid molecule or a plurality of nucleic acid molecules. They may therefore take the form of foreign nucleic acid molecules which encode 1-SST proteins and 1-FFT proteins in one nucleic acid molecule, but also nucleic acid molecules where the 1-SST-encoding nucleic acid sequences and the 1-FFT-encoding nucleic acid sequences are present on different nucleic acid molecules.

The nucleic acid sequences which encode a 1-SST protein and those which encode a 1-FFT protein can for example be present simultaneously in a vector, plasmid or linear nucleic acid molecule or, be components of two vectors, plasmids or linear nucleic acid molecules which are separate from one another.

If the nucleic acid sequences which encode a 1-SST protein and those which encode a 1-FFT protein are present in two nucleic acid molecules which are separate from one another, they can be introduced into the genome of the plant cell or plant either simultaneously ("cotransformation") or else in succession, i.e. one after the other ("supertransformation").

The nucleic acid molecules which are separate from one another can also be introduced into different individual sugarcane plant cells or sugarcane plants which are subsequently crossed with one another to give rise to sugarcane plants which simultaneously express a 1-SST and a 1-FFT.

Especially preferred in the context of the present invention is the combination of the *Cynara scolymus* 1-SST with the *Cynara scolymus* 1-FFT, the *Cynara scolymus* 1-SST with the *H. tuberosus* 1-FFT, the *H. tuberosus* 1-SST with the *C. solymus* 1-FFT or the *H. tuberosus* 1-SST with the *H. tuberosus* 1-FFT.

In a further embodiment of the present invention, the plant fructosyl transferase encodes a 6G-FFT protein which can utilize 1-kestose as fructosyl group donor in order to transfer a fructose unit to the glucose residue (glucose C6 carbon atom) of sucrose or to an existing oligofructan (for example of the neoinulin series), which is done by forming a beta-2,6-glycosidic bond. The transfer of fructose units to the glucose residue of sucrose leads to the formation of inulin of what is known as the neo-inulin series, such as, for example, of the trisaccharide neokestose (6G-kestotriose).

6G-FFT-encoding sequences from different organisms are known to the skilled worker and available for example under the following GenBank Accession numbers:

*Allium cepa* Y07838.1 (Vijn et al., Plant J. 11 (3), (1997), 387-398).

In a preferred embodiment of the method according to the invention, the *Allium cepa* 6G-FFT (SEQ ID No. 3) is used.

In a further embodiment of the present invention, the plant fructosyl transferase encodes a 6-SFT protein which forms the tetrasaccharide bifurcose (also referred to as 1,6-kestotetraose) from the trisaccharide 1-kestose and sucrose, which tetrasaccharide has an additional beta-2,6-linked fructose unit in comparison with 1-kestose. The involvement of 6-SFTs in the synthesis of longer-chained branched or unbranched levans is also being discussed (Vijn and Smeekens, Plant Physiology 120, (1999), 351-359). 6-SFTs catalyze the following reaction:

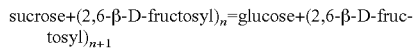

If sucrose is the only substrate on offer, 6-SFT catalyzes the formation of 6-kestotriose.

6-SFT-encoding sequences from different organisms are known to the skilled worker and available for example under the following GenBank Accession numbers:

*Triticum aestivum* AB029887.1 (Kawakami and Yoshida, Biosci. Biotechnol. Biochem. 66 (11), (2002), 2297-2305); *Poa secunda* AF192394.1 (Wei et al., J. Plant Physiol. 159(7), (2002), 705-715); *Agropyron cristatum* AF211253.1 (Wei and Chatterton, J. Plant Physiol. 158, (2001), 1203-1213).

In a preferred embodiment of the method according to the invention, the *Hordeum vulgare* 6-SFT (SEQ ID No. 4) is used.

The 1-SST, 1-FFT, 6G-FFT or 6-SFT proteins which are encoded by the foreign nucleic acid molecules share in each case certain characteristics. These may include for example biological activity, molecular weight, immunological reactivity, conformation, the presence of structural and/or functional domains or the like, and physical properties such as, for example, the migration behavior when gel electrophoreses are carried out, chromatographic behavior, sedimentation coefficients, solubility, spectroscopic properties, stability; pH optimum, temperature optimum or the like.

In a further embodiment of the method according to the invention, the 1-SST protein which is encoded by the foreign nucleic acid molecule employed has at least 40%, preferably at least 60%, especially preferably at least 80% and particularly preferably at least 90% identity with the 1-SST protein shown in SEQ ID No. 1.

In a further embodiment of the method according to the invention, the 1-FFT protein which is encoded by the foreign nucleic acid molecule employed has at least 40%, preferably at least 60%, especially preferably at least 80% and particularly preferably at least 90% identity with the 1-FFT protein shown in SEQ ID No. 2.

In a further embodiment of the method according to the invention, the 6G-FFT protein which is encoded by the foreign nucleic acid molecule employed has at least 70%, preferably at least 80%, especially preferably at least 90% and particularly preferably at least 95% identity with the 6G-FFT protein shown in SEQ ID No. 3.

In a further embodiment of the method according to the invention, the 6-SFT protein which is encoded by the foreign nucleic acid molecule employed has at least 50%, preferably at least 80%, especially preferably at least 90% and particularly preferably at least 95% identity with the 6-SFT protein shown in SEQ ID No. 4.

Using the sequence information stated in SEQ ID Nos. 1, 2, 3 or 4, the skilled worker is now able to isolate homologous sequences from other plant species. This can be done for example with the aid of conventional methods such as screening cDNA libraries or genomic libraries with suitable hybridization probes. The skilled worker knows that homologous sequences can also be isolated with the aid of (degenerate) oligonucleotides and using PCR-based methods.

Screening data bases as are provided for example by EMBL (available on the world wide web at ebi.ac.uk/Tools/index.htm) or NCBI (National Center for Biotechnology Information, available on the world wide web at ncbi.nlm.nih.gov/) can also be used for identifying homologous sequences.

Here, one or more sequences is, or are, set as query. This search sequence is then compared by computer programmes against known sequences which are described in the selected databases. Such database searches (for example blast or fasta searches) are known to the skilled worker.

If such a database search is carried out, for example at the NCBI (National Center for Biotechnology Information, available on the world wide web at ncbi.nlm.nih.gov/, National Center for Biotechnology Information National Library of Medicine, Building 38A, Bethesda, Md. 20894, USA), the standard settings which are set for the database search in question should be used.

For protein sequence alignments (blastp), these settings are as follows: limit entrez=not activated; filter=low complexity activated; expect value=10; word size=3; matrix=BLOSUM62; gap costs: existence=11, extension=1.

For nucleic acid sequence alignments (blastn), the following parameters are to be set: limit entrez=not activated; filter=low complexity activated; expect value=10; word size=11. In such a database search, for example the sequences described in SEQ ID Nos. 1, 2, 3 or 4 can be used as query sequence in order to identify homologous proteins which encode a 1-SST (SEQ ID No. 1), 1-FFT (SEQ ID No. 2), 6G-FFT (SEQ ID No. 3) or 6-SFT (SEQ ID No. 4).

In the context of the present invention, the term "identity" is intended to mean the number of identical amino acids (identity) with amino acids of other proteins, expressed in percent. The identity is preferably determined with the aid of computer programmes. If sequences which are compared with one another are different in length, the identity is to be determined in such a way that the number of amino acids which the shorter sequence shares with the longer sequence determines the percentage identity. Preferably, the identity is determined by means of the known and publicly available computer programmes ClustalW (Thompson et al., Nucleic Acids Research 22 (1994), 4673-4680).

ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW may likewise be downloaded from various Internet sites, inter alia at the IGBMC (Institut de Génétique et de Biologie Moléculaire et Cellulaire, B.P. 163, 67404 Illkirch Cedex, France; ftp://ftp-igbmc.u-strasbg.fr/pub/) and the EBI (ftp://ftp.ebi.ac.uk/pub/software/), and all mirrored Internet sites of the EBI (European Bioinformatics Institute, Wellcome Trust Genome Campus, Hinxton, Cambridge CB10 1SD, UK).

Preferably the ClustalW computer programme Version 1.8 is used to determine the identity. The following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS (OFF), NOPGAP, NOHGAP.

Identity further means that functional and/or structural equivalence exists between the respective proteins which are encoded by the foreign nucleic acid molecules. The proteins which are homologous to the proteins detailed in SEQ ID Nos. 1, 2, 3 or 4, and which thus constitute derivatives of these molecules which catalyze the same enzymatic reaction, can take the form of either naturally occurring variations, for example proteins from other plant species, or of mutations, it being possible for these mutations to have arisen naturally or by directed mutagenesis. These derivatives may furthermore take the form of synthetic sequences.

The foreign nucleic acid molecules can be any nucleic acid molecules, in particular DNA or RNA molecules, for example cDNA, genomic DNA, mRNA and the like. They can be naturally occurring molecules or else molecules generated by recombinant or chemico-synthetic methods. They can be single-stranded molecules which comprise either the coding or the noncoding strand, or else double-stranded molecules.

Sugarcane can be transformed by means of the gene gun (particle bombardment) (Bower and Birch, Plant Journal 2(3), (1992), 409-416; Franks and Birch, Aust. J. Plant Physiol. 18, (1991), 471-480; Gallo-Meagher and Irvine, Crop Science 36(5), (1996), 1367-1374; Bower et al., Molecular Breeding 2(3), (1996), 239-249; Snyman et al., S. Afr. J. Bot. 62(3), (1996), 151-154) or by agrobacterium-radiated gene transfer (Arencibia et al., Transgenic Research 7, (1998), An efficient protocol for sugarcane (*Saccharum* spp. L.) transformation mediated by *Agrobacterium tumefaciens*, 213-222).

The regeneration of sugarcane plants is also known to the skilled worker (see, for example, Bower and Birch, Plant Journal 2(3), (1992), 409-416; Gallo-Meagher and Irvine, Crop Science 36(5), (1996), 1367-1374; Bower et al., Molecular Breeding 2(3), (1996), 239-249; Ho and Vasil, Ann. Bot. 51, (1983), 719-726).

To express the foreign nucleic acid molecules encoding a fructosyl transferase in sugarcane plants, these molecules are preferably linked with regulatory DNA sequences which ensure the transcription in plant cells. These include in particular promoters. In principle, any promoter which is active in sugarcane plants/plant cells is suitable for the expression.

The promoter may be chosen in such a way that expression takes place constitutively or only in a particular tissue, a particular point in time of the plant's development or at a point in time which is determined by external factors. The promoter can be homologous or heterologous, both with regard to the plant and with regard to the foreign nucleic acid molecule.

Examples of suitable constitutive promoters are the promoters of the cauliflower mosaic virus 35S RNA, known as the 35S promoter (Odell et al., 1985, Nature, 313, 810-812) and the maize ubiquitin promoter (Christensen et al., Plant Mol. Biol. 18, (1992), 675-689) or the rice ubiquitin promoter (Liu et al., Plant Science 165, (2003), High transgene expression levels in sugarcane (*Saccharum officinarum* L.) driven by the rice ubiquitin promoter RUBQ2, 743-750).

Furthermore, it is possible to employ promoters which may mediate gene expression in the stem of sugarcane, such as, for example, the banana streak badna virus promoter (Schenk et al., Plant Mol. Biol. 47, (200/1), 399-412).

Furthermore, a termination sequence (polyadenylation signal), which serves for adding a poly-A tail to the transcript, may be present. The poly-A tail is thought to have a function in stabilizing the transcript. Such elements are described in the literature (cf. Gielen et al., EMBO J. 8 (1989), 23-29) and can be substituted as desired.

Intron sequences between the promoter and the coding region may also be present. Such intron sequences can lead to expression stability and to elevated expression in plants (Canis et al., 1987, Genes Devel. 1, 1183-1200; Luehrsen and Walbot, 1991, Mol. Gen. Genet. 225, 81-93; Rethmeier, et al., 1997; Plant Journal. 12(4):895-899; Rose and Beliakoff, 2000, Plant Physiol. 122(2), 535-542; Vasil et al., 1989, Plant Physiol. 91, 1575-1579; XU et al., 2003, Science in China Series C Vol. 46 No. 6, 561-569). Examples of suitable intron sequences are the first intron of the maize sh-1 gene (Werr et al., EMBO J. 4, (1985), 1373-1380), the first intron of the maize poly-ubiquitin gene 1 (Christensen et al., Plant Mol. Biol. 18, (1992), 675-689), the intron of the rice actin gene (McElroy et al., Plant Cell 2, (1990), Isolation of an efficient actin promoter for use in rice transformation, 163-172), or one of the first two introns of the *Arabidopsis* PAT1 gene (Rose and Last, Plant J. 11, (1997), Introns act post-transcriptionally to increase expression of the *Arabidopsis thaliana* tryptophan pathway gene PAT1, 455-464).

Methods to be Used in the Context of the Present Invention:

1. Sampling for the Fructan and Sugar Determination

Stalks of sugarcane plants which are 12 to 15 months old and have more than 10 internodes are harvested. After all of the leaves have been removed, the internodes of the stalk are numbered from top (=1) to bottom (for example =36). A stalk disc approximately 1-2 g in weight is excised from the middle of each internode. The stalk discs of 3 internodes are then combined to give one sample and frozen in liquid nitrogen.

For the sugar and fructan extraction, the stalk discs are first comminuted in a Waring blender (from Waring, New Hartford, Conn., USA). The sugars and the fructan are extracted by shaking for one hour at 95° C. in 10 mM sodium phosphate buffer pH 7.0. Thereafter, the solids are removed by filtration through a 30 µm sieve. The resulting solution is subsequently employed for the fructan and sugar determination (see herein below).

2. Fructan Determination

The fructan content of the solution obtained by the sugar and fructan extraction (see Method 1) was determined by means of the "Fructan Assay Procedure" kit from Megazyme. The principle of this assay is based on the hydrolysis of the fructan into its reducing monomers glucose and fructose and subsequent photometric determination (wavelength=410 nm) of the content of these reducing sugars (glucose, fructose) after staining with what is known as the "PAHBAH method" (for details on this method, see herein below).

In a first step, the sucrose present in the extract is hydrolyzed by the specific enzyme sucrase to give glucose and fructose. Furthermore, starches and maltodextrins present in the extract are degraded with a mixture of the highly purified enzymes β-amylase, pullulanase and maltase, likewise to give glucose. Thereafter, the resulting reducing sugars are reduced to sugar alcohols with treatment with alkaline borohydride solution and thus removed from the solution. The solution is neutralized and excess borohydride is removed by addition of dilute acetic acid. Thereafter, the fructan is hydrolyzed with purified fructanase (exo-inulinase) to give fructose and glucose, and the content of the resulting monosaccharides is determined by the PAHBAH method.

Chemicals and Solutions in the Kit:
1. 50 U sucrase (yeast), 500 U β-amylase (*B. cereus*), 100 U pullulanase (*K. pneumoniae*) and 1000 U maltase (yeast) are present as a lyophilized powder; for the measurement, the are dissolved in 22 ml of 0.1 M sodium maleate buffer pH 6.5 (herein below referred to as "enzymes 1").
2. 8000 U fructanase are present in the form of a lyophilized powder; for the measurement, they are dissolved in 22 ml of 0.1 M sodium acetate buffer pH 4.5 (herein below referred to as "enzymes 2").
3. fructose standard solution (1.5 mg fructose/ml), dissolved in 0.2% benzoic acid.
4. fructan control
   chloroform-washed Jerusalem artichoke powder (*Helianthus tuberosus*) with a known fructan content Solutions not Present in the Kit:
I. PAHBAH reagent
   Solution A: 10 g of PAHBAH (p-hydroxybenzoic hydrazide, Sigma Bestell No. H-9882) are added to 60 ml of distilled water in a 250 ml glass beaker, and 10 ml of concentrated hydrochloric acid is added to the suspension, with stirring. The solution is made up to 200 ml and stored at room temperature.
   Solution B: firstly, 24.9 g of tri-sodium citrate, then 2.20 g of calcium chloride and filially 40 g of sodium hydroxide are dissolved in 500 ml of distilled water, with stirring. After the addition of sodium hydroxide, the solution may be opaque, but turns clear when the solution is made up to 2 l with water. The solution is stored at room temperature.
   Shortly prior to use, 20 ml of solution A are added to 180 ml of solution B and mixed thoroughly (=PAHBAH reagent). The solution must be stored on ice and can be used for 4 hours.
II. 50 mM sodium hydroxide solution
III. alkaline sodium borohydride solution 10 mg/ml sodium borohydride (Sigma, Bestell No. S-9125) in 50 mM sodium hydroxide
IV. 100 mM acetic acid Detection Method:
1. 20 mg of the fructan control sample are extracted in 1 ml of distilled water for 1 hour in a heating block at 95° C. After centrifugation (5 minutes at 13000×g), the supernatant is transferred to a fresh reaction vessel and the precipitate is again taken up in 1 ml of distilled water and extracted for 1 hour in a heating block at 5° C. After recentrifugation (see above), the supernatant is removed and combined with the first supernatant.
2. 200 µl of sample (extract, fructan standard and fructan control) are mixed with 200 µl of enzyme µl and incubated for 40 minutes at 40° C. (incubation time 10 minutes longer than stated in the Megazyme protocol).
3. 200 µl of alkaline sodium borohydride solution are added, and the solution is mixed thoroughly and incubated for 30 minutes at 40° C. to achieve complete conversion of the reducing sugars into sugar alcohols.
4. By addition of 500 µl of 100 mM acetic acid and mixing thoroughly, the excess borohydride is removed and the solution is brought to pH=4.5.
5. 200 µl aliquots of the solution are mixed with 100 µl of enzymes 2 and incubated for 60 minutes at 40° C. (40 minutes longer than the incubation time stated in the Megazyme kit to achieve complete hydrolysis of the fructan).
6. A fructose standard is tested simultaneously as further sample. 200 µl of the fructose standard solution present in the kit is treated with 900 µl of 100 mM sodium acetate buffer pH 4.5 and mixed. 4×200 µl of this mixture are removed and treated with a further 100 µl of 100 mM sodium acetate buffer pH 4.5.
7. All samples and an additional blank sample (300 µl of 100 mM sodium acetate buffer pH 4.5) were mixed with 5 ml of PAHBAH reagent and the mixture was incubated for exactly 6 minutes in a boiling water bath.
8. Thereafter, the samples are immediately cooled for about 5 minutes in cold water (10-15° C.).
9. The absorption of all solutions is measured in a spectrophotometer at a wavelength of 410 nm against the blank sample.

The following equation is used for the calculation:

$$\text{fructan } (\% \ w/w) = \Delta E \times F \times 5 \times V_{Ex} 1.1/0.2 \times 100/W \times 1/1000 \times 162/180$$

$\Delta E$=PAHBAH absorption of the sample is measured against the blank sample
$F$=factor for converting the fructose absorption into µg fructose (54.5 µg fructose/absorption)=
5=factor for the conversion of 200 µl to 1 ml incubation volume
$V_{Ex}$=extract volume
1.1/0.2=0.2 ml of the total 1.1 ml of the enzyme digest was used for the analysis
100/W=factor indicating fructan in % of the weight (W)
1/1000=conversion from µg into mg
162/180=factor for converting the free fructose measured into fructan-bound fructose 3. Sugar Determination (Glucose, Fructose and Sucrose)

The glucose, fructose and sucrose contents in the extract obtained in accordance with method 1 is determined photometrically in an enzyme assay via the conversion of $NAD^+$ (nicotinamide adenine dinucleotide) into NADH (reduced nicotinamide adenine dinucleotide). During the reduction, the aromatic character at the nicotinamide ring is lost, and the absorption spectrum thus changes. This change in the absorption spectrum can be detected photometrically. The glucose and fructose present in the extract is converted into glucose-6-phosphate and fructose-6-phosphate by means of the enzyme hexokinase and adenosin triphosphate (ATP). The glucose-6-phosphate is subsequently oxidized by the enzyme glucose-6-phosphate dehydrogenase to give 6-phosphogluconate. In this reaction, $NAD^+$ is reduced to give NADH, and the amount of NADH formed is determined photometrically. The ratio between the NADH formed and the glucose present in the extract is 1:1, so that the glucose content can be calculated from the NADH content using the molar absorption coefficient of NADH (6.3 l $mmol^{-1}$ $cm^{-1}$). Following the complete oxidation of glucose-6-phosphate, fructose-6-phosphate, which has likewise formed in the solution, is converted by the enzyme phosphoglucoisomerase to give glucose-6-phosphate which, in turn, is oxidized to give 6-phosphogluconate. Again, the ratio between fructose and the amount of NADH formed is 1:1. Thereafter, the sucrose present in the extract is cleaved by the enzyme sucrase (Megazyme) to give glucose and fructose. The glucose and fructose molecules liberated are then converted with the abovementioned enzymes in the NAD$^+$ dependent reaction to give 6-phosphogluconate. The conversion of one sucrose molecule into 6-phosphogluconate results in two NADH molecules. The amount of NADH formed is likewise determined photometrically and used for calculating the sucrose content, using the molar absorption coefficient of NADH.

4. Determination of the Total Carbohydrate Content

The total carbohydrate content is determined by adding the glucose, fructose, sucrose and fructan contents.

5. Determination of the Storage Carbohydrate Content

The storage carbohydrate content is determined by adding the sucrose and fructan contents.

EXAMPLE 1

Generation of Transgenic Sugarcane Plants which Express a 1-sst Gene from Artichoke (*Cynara scolymus*) (pML1 Plants)

Using the PCR primers P5 (5'-aattcagctgttatccctaggcg-gacc-3') (SEQ ID No. 5) and P7 (5'-agtcagctgggaatttaaatttaat-taaggcg-3') (SEQ ID No. 6), a 262 bp fragment on the vector pMCS5 (MoBiTec GmbH, Gottingen, Germany) was amplified (1.5 mM MgCl$_2$, 25 cycles of in each case 30 seconds at 94° C., 30 seconds at 58° C., 30 seconds at 72° C., 1 U TaqI polymerase/50 µl), and the PCR product was cut with PvuII and cloned into the PvuII-cut vector pSK(−)(Stratagene). The resulting vector was named pSK(−)-MCS. Two PCR products were combined to give the finished vector. The first fragment was obtained by amplification of a 1266 bp fragment on pSK(−)-MCS using the primers P5 (see above) and P6 (5'-ggtaactgtcagaccaagtttac-3') (SEQ ID No. 11) (1.5 mM MgCl$_2$, 30 cycles of in each case 15 seconds at 94° C., 15 seconds at 60° C., 15 seconds at 72° C., 1 U PwoI polymerase/ 50 µl). The second PCR product, which comprised the asd gene (Haziza et al. EMBO J. 1, 1982, 379-384; GenBank Accession No. V00262.1), was amplified on *E. coli* DNA using the primers Asd1 (AAA ATT TAA ACA TAA TCA ggA TCA ATA AAA C) (SEQ ID No. 7) and Asd2 (AAA ATT TAA ACA TCT gCg CTT ACT CCT) (SEQ ID No. 8) (1.5 mM MgCl$_2$, 25 cycles of in each case 30 seconds at 94° C., 30 seconds at 60° C., 1 minute at 72° C., 1 U TaqI polymerase/50 µl) and recut with DraI. The two fragments were ligated. The resulting plasmid was named pML11.

All plasmids which carry the asd gene as selection marker were propagated in G6MD2 cells (Schwartz, M., J. Biol. Chem. 92, (1966), 1083-1089) and selected on medium without diaminopimelic acid.

Two fragments were ligated simultaneously into the BglII-opened pMCS5 vector. Fragment 1 comprised the *Agrobacterium tumefaciens* nos terminator (Depicker et al., 1982, Journal of Molecular and Applied Genetics 1, 561-573) and was amplified on pBinAR using the primers P9 (ACT TCT gCA gCg gCC gCg ATC gTT CAA ACA TTT ggC AAT AAA gTT TC) (SEQ ID No. 9) and P10 (TCT AAg CTT ggC gCC gCT AgC AgA TCT gAT CTA gTA ACA TAg ATg ACA CC) (SEQ ID No. 10) (1.5 mM MgCl$_2$, 25 cycles with in each case 30 seconds at 94° C., 30 seconds at 60° C., 30 seconds at 72° C., 1 U PwoI polymerase/50 µl) and recut with Bg/II and PvuI. Fragment 2 was obtained from plasmid pBinAR by digestion with Bg/II and PvuI. The 2674 bp fragment comprised the *Agrobacterium tumefaciens* nos promoter (Depicker et al., Journal of Molecular and Applied Genetics 1, 1982, 561-573) and the open reading frame of the *E. coli* nptII gene (Beck et al. Gene 19, 1982, 327-336; Gen-Bank Accession No. V00618). The two fragments were cloned simultaneously into the BglII-cut pMCS5 (MoBiTec), and a plasmid which comprised in each case one of the two fragments was selected. The resulting plasmid was named pML7.

To remove the NotI cleavage site in the vector pMCS5 (MoBiTec GmbH, Göttingen, Germany), the vector was cut with the restriction enzymes BamHI and Bg/II and the vector was religated. The resulting plasmid was named pML4. The *Agrobacterium tumefaciens* nos terminator (see herein above) was cloned into the resulting vector between the restriction cleavage sites HindIII and PstI. To this end, a corresponding DNA fragment was amplified on pBinAR (see herein above) using the primers P9 (ACT TCT gCA gCg gCC gCg ATC gTT CAA ACA TTT ggC AAT AAA gTT TC) (SEQ ID No. 9) and P10 (TCT AAg CTT ggC gCC gCT AgC AgA TCT gAT CTA gTA ACA TAg ATg ACA CC) (SEQ ID No. 10) and recut with HindIII and PstI. The resulting vector was named pML54-nos. A 1986 bp PstI fragment which comprised the *Zea mays* ubiquitin promoter (Gen-Bank Accession 94464, Christensen et al., Plant Mol. Biol. 18, 1992, 675) and the first intron of the same gene, which intron had been truncated by digestion with ClaI and religation, was cloned into the PstI cleavage site of pML54-nos. The 3' terminus of this fragment was orientated in the nos terminator direction in the resulting vector. The resulting plasmid was named pML8.

An NotI fragment from the vector pCy21 was cloned into pML8, which fragment comprises the open reading frame of the *Cynara scolymus* sucrose-sucrose 1-fructosyl transferase (1-SST) (Hellwege et al., Plant Journal 12, 1997, 1057-1065; Genbank Accession Y09662.1). The resulting plasmid was named pML10.

The vector pML11 was cut with NarI and ligated with a 4048 bp NarI fragment from pML10. The resulting plasmid is referred to as pML11-SST. It was cut with AvrII and a 2068 bp fragment from pML7, which fragment had been obtained by restriction digest with XbaI and SpeI was cloned. The resulting vector is referred to as pML1.

Transformation of Sugarcane Plants with the 1-sst Construct (pML1)

The induction of callus and the transformation of sugarcane were carried out by the method of Snyman et al. (Snyman et al., 1996, S. Afr. J. Bot 62, 151-154). The pML1 construct was cotransformed with the vector pEmuKN, which expressed the nptII gene (Beck et al. Gene 19, 1982, 327-336; Gen-Bank Accession No. V00618) under the control of the pEmu promoter (Last et al. (1991) Theor. Appl. Genet. 81, 581-588). Plants were regenerated by the method of Snyman et al. 2001 (Acta Horticulturae 560, (2001), 105-108).

EXAMPLE 2

Transgenic Sugarcane Plants Transformed with the 1-sst Gene from Artichoke (*Cynara scolymus*) (pML1 Plants)

2.1 Materials and Methods

Sugarcane plants of the line NCo310 were transformed with the artichoke sst gene as described in Example 1 by means of particle gun bombardment. Transgenic sugarcane plants of the oligofructan-synthetizing line 2-1-5-3 and the wild-type line NCo310 were grown in the greenhouse. Stalks were harvested from approximately 12-month old plants. After removal of the leaves, the internodes of the stalk were numbered from top (=1) to bottom (for example =36). A stalk disc approximately 1-2 g in weight was excised from the middle of each internode. The stalk discs of 3 internodes were combined to give one sample and frozen.

The method described in greater detail in the methodology section was employed for the extraction of sugar and fructan.

2.2 Results

Sugarcane plants cv. NCo310 which had been transformed with the artichoke sst gene and store the oligofructans kestose and nystose in addition to sucrose have a higher storage carbohydrate content and a higher total carbohydrate content in the stalks in comparison with NCo310 control plants (see Table 1).

TABLE 1

Determination of the total carbohydrate content (glucose + fructose + sucrose + fructan) in the stalks of sugarcane plants; NCo310 = wild-type control, 2-1-5-3 = NCo310 sugarcane plant transformed with the artichoke (*Cynara scolymus*) sst gene; the numbering "1", "2", "3" and "4" refers to samples taken from four different stalks of transgenic event 2-1-5-3.

| Sample  |   | Fresh weight [g] | Suc. + fructan [mg/g FW] | Total carbohydrates [mg/g FW] |
|---------|---|------------------|--------------------------|-------------------------------|
| NCo310  |   | 1008             | 105                      | 109                           |
| 2-1-5-3 | 1 | 1134             | 170                      | 175                           |
|         | 2 | 945              | 116                      | 124                           |
|         | 3 | 1069             | 170                      | 175                           |
|         | 4 | 920              | 173                      | 180                           |

A rise in the sucrose content of internode 1-3 to internode 10-12 can be observed in the uppermost internodes of the stalk of the wild-type plant NCo310. Sucrose storage is at its maximum in the further internodes (>12). In these stalk segments, the sucrose content varies between 10-14% of the fresh weight. Fructans cannot be detected in sugarcane wild-type plants.

In the stalk of the transgenic plants 2-1-5-3, too, the storage carbohydrate (sucrose and fructan) content climbs from internode 1-3 to internode 7-9 and reaches saturation thereafter. Surprisingly, markedly higher storage carbohydrate contents than in the corresponding wild-type plants, namely 15-26% of the fresh weight, are obtained in the lower segments of the transgenic stalks.

Thus, the expression of the artichoke sst gene in sugarcane leads in total to a significant increase in storage carbohydrates in the sugarcane plants. If the sucrose contents of the wild-type plants (NCo310) are compared with those of the 1-SST expressing transgenic sugarcane plants (2-1-5-3), the following results are obtained:

TABLE 2

Sucrose content in sugarcane stalks of the wild type NCo310 and of the transgenic oligofructan-synthetizing line 2-1-5-3; the numbering "1", "2", "3" and "4" refers to samples taken from four different stalks of transgenic event 2-1-5-3.

| Sample  |   | Sucrose content [mg/g FW] | Sucrose [% of wild type] |
|---------|---|---------------------------|--------------------------|
| NCo310  |   | 105                       | 100                      |
| 2-1-5-3 | 1 | 126                       | 120                      |
|         | 2 | 86                        | 82                       |
|         | 3 | 122                       | 116                      |
|         | 4 | 123                       | 113                      |

The mean of the sucrose contents determined for the individual internode sections was determined. The sucrose content in the wild type was set as 100% and the sucrose contents in the transgenic line are in relation to the wild type.

EXAMPLE 3

Generation of Transgenic Sugarcane Plants which Express a 1-sst Gene and a 1-fft Gene from Artichoke (*Cynara scolymus*) (pML2 Plants)

The vector pML11 which has been described in Example 1 was used as basic vector for cloning the construct comprising the 1-sst and the 1-fft from artichoke.

1. Expression Cassette for the 1-fft Gene

An NotI fragment from pCy3 comprising the open reading frame of the *Cynara scolymus* fructan-fructan 1-fructosyl transferase (fft) (Hellwege et al., FEBS Lett. 427, 1998, 25-28; Accession number AJ000481.2) was doned into the vector pML8 (see Example 1). The resulting plasmid was named pML9.

2. Final Vector

The vector pML11 was cut with NheI and ligated to a 3877 bp NheI fragment from pML9. The NheI fragment from pML9 was obtained by a partial digest and comprises the complete expression cassette for 1-fft (ubiquitin promoter, ubiquitin intron, open reading frame for fft and nos terminator). In the resulting vector, the 1-fft cassette was in the same orientation as the asd gene. The resulting plasmid is named pML11-FFT. This plasmid was cut with NarI and ligated to a 4048 by NarI fragment from pML10, the 1-sst cassette in the vector being in the same orientation as the 1-fft cassette. The resulting plasmid was named pML11F+S. It was cut with AvrII and a 2068 bp fragment from pML7, which fragment had been obtained by restriction digest with XbaI and SpeI, was cloned. The inserted cassette was in the same orientation as the 1-sst and the 1-fft cassette. The resulting vector was named pML2 and used for generating transgenic sugarcane plants which express the 1-SST and the 1-FFT gene from *Cynara scolymus*. The transformation and regeneration of sugarcane were carried out analogously to the methods described in Example 1 using the vector pEmuKN.

EXAMPLE 4

Transgenic Sugarcane Plants Transformed with the 1-sst and the 1-fft Gene from Artichoke (pML2 Plants)

1.1 Materials

The transgenic sugarcane plants which had been generated as described in Example 3 and which express both the 1-SST and the 1-FFT gene from *Cynara scolymus* were grown in the greenhouse for 12 months. In each case one sugarcane stalk of the transgenic line 1-2-3-3 and a wild-type sugarcane plant was defoliated, the stalk was divided into segments of 3 internodes, and these internode segments were frozen in liquid nitrogen in a sealed 50 ml plastic container. The fresh weight of the samples was determined. The extraction for the purposes of the fructan and sugar determination was as described in the methodology section.

1.2 Results

The sugarcane stalks were divided into segments of in each case three internodes, as specified above. The internodes were numbered from top to bottom (top=internode 1, bottom=internode 21).

In the sugarcane wild-type plant, the sucrose contents rose from internode 1-3 up to internode 10-12. The sucrose contents of all subsequent internodes were similarly high (13-15% of the fresh weight). The mean sucrose content in the sugarcane wild-type plant was 121 mg/g fresh weight.

In the transgenic line 1-2-3-3, which comprises the sst and the fft gene from artichoke and which accumulates inulin, the storage carbohydrate content in the stalk likewise climbs from internode 4-6 to internode 10-12 and varies in the bottom-most internodes (>12) between 17 and 19% of the fresh weight. The mean storage carbohydrate content is 166 mg/g fresh weight, which is higher than the sucrose content in the sugarcane wild-type plants.

Figure 2:
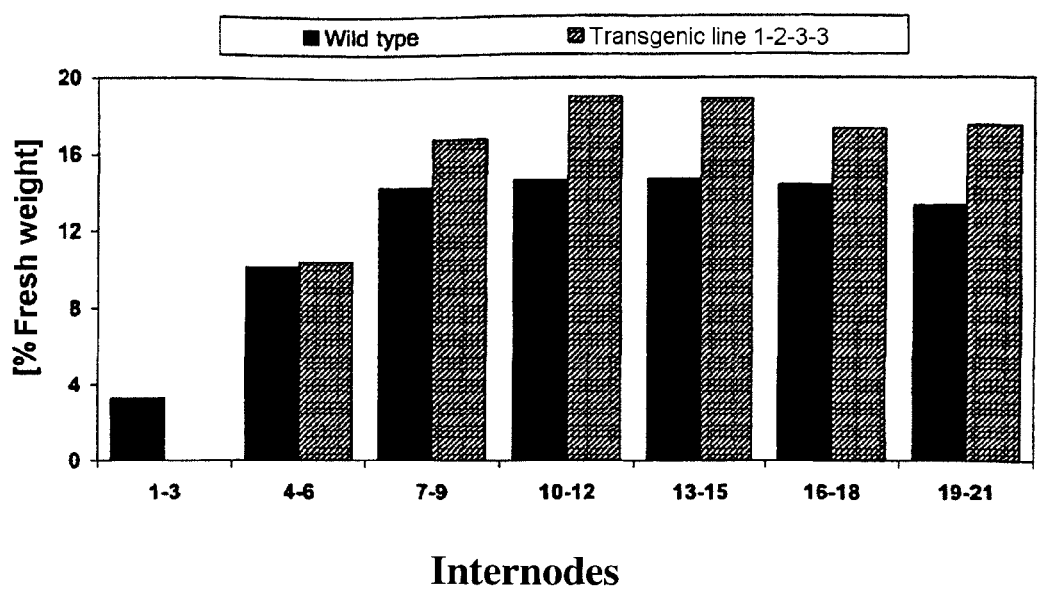
FIG. 2: Storage carbohydrate (sucrose and fructan) content in sugarcane stalks of the wild type NCo310 and of the transgenic fructan-synthetizing line 1-2-3-3. Material of three adjacent internodes was combined to give one sample.

In total, it can be observed that, surprisingly, the storage carbohydrate (sucrose+fructan) content in the internodes of the transgenic sugarcane line 1-2-3-3 is higher in all internodes analyzed than in those of the wild type. This difference is reflected in the mean storage carbohydrate content in the complete plant (Table 2) and in the storage carbohydrate content per internode (FIG. 2). The simultaneous expression of the 1-sst and the 1-fft gene from artichoke in sugarcane thus leads in total to an increase in storage carbohydrates in the genetically modified sugarcane plants in comparison with the sugarcane wild-type plants.

TABLE 3

Mean storage carbohydrate content in the sugarcane stalk of the wild-type line NCo310 and the transgenic fructan-accumulating line 1-2-3-3.

|  | Sucrose + fructan [mg/g FW] |
|---|---|
| Wild type | 121 |
| 1-2-3-3 | 166 |

If the sucrose contents of the wild-type plants (NCo310) are compared with those of the 1-2-3-3 plants, the following results are obtained:

TABLE 4

Sucrose content in the wild type NCo310 and of the transgenic fructan-synthetizing line 1-2-3-3.

| Sample | Sucrose content [mg/g FW] | Sucrose [% wild type] |
|---|---|---|
| Wild type | 121 | 100 |
| 1-2-3-3 | 41 | 34 |

The mean of the sucrose contents determined for the individual internode segments was determined, the mean sucrose content of the wild type was set as 100%, and the sucrose content in the transgenic line was expressed in relation thereto.

We claim:
1. A method for increasing the storage carbohydrate content of a sugarcane plant comprising
genetically modifying a sugarcane plant by introducing a nucleic acid molecule encoding the amino acid sequence of SEQ ID NO: 1 and a nucleic acid molecule encoding the amino acid sequence of SEQ ID NO: 2; wherein said genetically modified sugarcane plant has an increased storage carbohydrate content in comparison with corresponding non-genetically-modified sugarcane wild-type plants.

* * * * *